United States Patent [19]

Itoh et al.

[11] Patent Number: 4,906,665
[45] Date of Patent: Mar. 6, 1990

[54] HYDROXYALKYLCYSTEINE DERIVATIVE AND EXPECTORANT CONTAINING THE SAME

[75] Inventors: Yoshikuni Itoh; Hiroyuki Mizuno, both of Tomisato; Chikako Kiyohara, Narashino; Susumu Sato, Shisui; Tatsuhiko Katori, Tone, all of Japan

[73] Assignee: SS Pharmaceutical Co., Ltd., Tokyo, Japan

[21] Appl. No.: 365,371

[22] Filed: Jun. 13, 1989

[30] Foreign Application Priority Data

Jun. 16, 1988 [JP]   Japan ................................. 63-148653

[51] Int. Cl.$^4$ ..................... A01N 31/02; A01N 33/08; C07C 149/247
[52] U.S. Cl. .................................... 514/562; 514/855; 562/556
[58] Field of Search ................. 562/556; 514/562, 855

[56] References Cited

U.S. PATENT DOCUMENTS

| | | | |
|---|---|---|---|
| 3,326,762 | 6/1967 | Joullié et al. | 514/562 |
| 3,892,852 | 7/1975 | Joullié et al. | 560/153 |
| 4,243,679 | 1/1981 | Adsara et al. | 562/557 |
| 4,618,625 | 10/1986 | Vinas | 514/494 |

Primary Examiner—Donald B. Moyer
Assistant Examiner—Karen E. Plue
Attorney, Agent, or Firm—Oblon, Spivak, McClelland, Maier & Neustadt

[57] ABSTRACT

Novel hydroxyalkylcysteine derivatives of the following formula (I) and an expectorant comprising the same are disclosed.

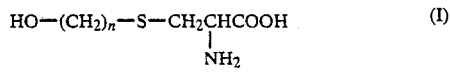

(I)

wherein n represents an integer of 5 to 24. The expectorant is stabile, has little side effects and toxicity, and exhibits an excellent expectorant effect.

2 Claims, No Drawings

HYDROXYALKYLCYSTEINE DERIVATIVE AND EXPECTORANT CONTAINING THE SAME

BACKGROUND OF THE INVENTION

1. Field of the Invention:

The present invention relates to a novel hydroxyalkylcysteine derivative and an expectorant comprising the hydroxyalkylcysteine derivative as an active ingredient.

2. Description of the Background:

Up to the present time, S-(2-hydroxyethyl)-L-cysteine [Journal of Pharmaceutical Sciences, 50, 312 (1961)] and S-(3-hydroxypropyl)-L-cysteine [Biochem. J., 100, 362 (1966)] are known as hydroxyalkylcysteine derivatives. However, all that has been reported concerning their pharmacological effects is that S-(2-hydroxyethyl)-L-cysteine has anti-seborrheic activity (West German Laid-open Patent No. 2,219,726) and that S-(3-hydroxypropyl)-L-cysteine is effective against anti-cholesterolemia and arteriosclerosis (U.S. Pat. No. 3,892,852).

On the other hand, cysteine derivatives such as carbocysteine, N-acetylcysteine, cysteine ethyl ester hydrochloride, and the like are being used as expectorants.

The cysteine derivatives described above when used in expectorants are not completely satisfactory, particularly both N-acetylcysteine and ethyl ester hydrochloride have the problems of strong toxicity and chemical instability.

Therefore, the development of an expectorant possessing stability, little side effects and toxicity, as well as an excellent expectorant effect, has been desired.

In view of such circumstances, the inventors of the present invention synthesized a number of compounds and examined their pharmacological effects. As a result of these investigations, it was found that the hydroxyalkylcysteine derivative shown by the following formula (I) fulfilled the above conditions and possessed an excellent expectorant effect.

SUMMARY OF THE INVENTION

Accordingly, an object of the present invention is to provide a hydroxyalkylcysteine derivative represented by the following formula (I), $$HO-(CH_2)_n-S-CH_2CHCOOH \quad \quad (I)$$
$$\qquad\qquad\qquad\qquad\qquad |$$
$$\qquad\qquad\qquad\qquad\qquad NH_2$$

wherein n represents an integer of 5 to 24.

Another object of the present invention is to provide an expectorant comprising a hydroxyalkylcysteine derivative represented by said formula (I) as an active ingredient.

Other objects, features and advantages of the invention will hereinafter become more readily apparent from the following description.

DETAILED DESCRIPTION OF THE INVENTION AND PREFERRED EMBODIMENTS

In formula (I) above, n is an integer between 5 and 24, preferably between 5 and 10, and most preferably between 5 and 7.

Compound (I) of the present invention is prepared by the reaction involving a substituted alkyl alcohol (II) and cysteine (III) according to the following reaction formula, $$X-(CH_2)_n-OH + HS-CH_2-CH-COOH \longrightarrow$$
$$\qquad\qquad\qquad\qquad\qquad\qquad\qquad |$$
$$\qquad\qquad\qquad\qquad\qquad\qquad\qquad NH_2$$
$$\quad (II) \qquad\qquad\qquad (III)$$

$$HO-(CH_2)_n-S-CH_2CHCOOH$$
$$\qquad\qquad\qquad\qquad\qquad |$$
$$\qquad\qquad\qquad\qquad\qquad NH_2$$
$$\qquad\qquad (I)$$

wherein X represents a halogen atom, a tosyloxy group, or a methanesulfonyloxy group, and n is an integer defined above.

This method is carried out by reacting 1 mol of a compound (III) per 1–1.2 mols of a compound (II) for 4–24 hours in an appropriate solvent at a pH of about 9 using an alkali at room temperature, or if required, with heating.

Sodium bicarbonate, potassium carbonate, sodium carbonate, potassium hydroxide, or sodium hydroxide can be used as an alkali. Water, a water-methanol solvent, or a water-ethanol solvent are desirable as the solvent.

After the reaction is completed, the reaction mixture is washed with an organic solvent (ether, ethyl acetate, chloroform, methylene chloride, or the like) and the pH of the aqueous layer is adjusted to between 4 and 5 using hydrochloric acid or the like. If crystals precipitate out, they are collected by filtration and refined by recrystallization, or the like. In the case where the crystals do not precipitate out, the aqueous layer is concentrated under reduced pressure and the residue is extracted using absolute methanol or the like. After concentrating the extract, ether is added to precipitate crystals, which are then purified by recrystallization or the like. Alternatively, crystals are produced from the residue with acetone and then purified by ion-exchange column chromatography or by recrystallization. Compound (I) of the present invention is obtained using these methods.

Hereinafter are presented experimental examples to illustrate the expectorant effect of Compound (I) of the present invention. These examples are given for illustration of the invention and are not intended to be limiting thereof.

EXPERIMENTAL EXAMPLES

Test Method:

The expectorant effect was investigated based on the method of Sakuno [Manchurian Medical Journal, 33, 779 (1940)].

The test compound was suspended or dissolved in an aqueous solution of 0.5 % carboxymethylcellulose sodium (CMC-Na). The solution was administered orally to rabbits at 500 mg/kg. At the same time, 1 mg/kg of a 0.6% phenol-sulfonphthalein (PSP) injection solution was administered into the ear vein of the rabbits. Thirty minutes later, the carotid artery was severed and the rabbits were sacrificed by exsanguination. A cannula was placed into the trachea and a heated (38° C.) aqueous solution of 5% sodium bicarbonate (12.5 ml/kg) was infused through cannula. After leaving for 10 mitutes, the infused solution was slowly drawn out and then infused again. This procedure was repeated a total of 3 times. The final solution collected was centrifuged at 10,000 rpm for 30 minutes at 4° C. After adjusting the pH of the supernatant thus obtained to 8.0 with 1 N hydrochloric acid. the absorbance was measured using a spectrophotometer at a wavelength of 557 nm in order to assay the amount of PSP. The amount of PSP was measured in the same way as described above in the control group after orally administering 10 ml/kg of an aqueous solution of 0.5% CMC-Na. The expectorant effect of the test compound was judged by the rate of increase in the amount of PSP which effused into the respiratory tract.

The rate of increase in PSP amount was calculated according to the following formula, Rate of increase in PSP amount
(%)=(S−C)/C×100 wherein S is the amount of PSP in the test compound group and C is the amount of PSP in the group given 0.5% CMC-Na (control group).

Test Results:

The results are presented in Table 1.

TABLE 1

| Test compound | PSP concentration ($\mu$g/ml) | Rate of increase in PSP (%) |
| --- | --- | --- |
| Compound 1 | 0.91 | 98 |
| Compound 2 | 0.80 | 75 |
| Carbocysteine | 0.57 | 23 |
| Control | 0.46 | — |

Compound 1: S—(5-hydroxypentyl)-L-cysteine
Compound 2: S—(6-hydroxyhexyl)-L-cysteine As can be seen from Table 1, compared to the control group, rabbits to which Compound (I) was given showed a significant increase in the amount of PSP in the airway, thus evidencing that the compounds of this invention possess an excellent expectorant effect.

In addition, the toxicity of the compounds of formula (I) was extremely low. In particular, the values for acute toxicity ($LD_{50}$) of the Compound (I) in which n = 5 in formula (I) were greater than 10 g/kg when orally administered to mice or rats.

When Compound (I) is used as an expectorant the dose is different depending upon the administration route or the symptoms. However, in the case of oral administration in normal adults, a daily administration of 0.1–5 g once or over several doses is desirable, while for non-oral administration, the daily dose range is 0.02–1 g, also either given as a single dose or over several doses.

The present expectorant can be given by either oral or non-oral administration in any type of preparations. For oral administration forms such as tablets, capsules, powders, granules, troches or liquids, and the like can be used. For non-oral preparations hypodermic injections, intramuscular or intravenous injections, mixed transfusion or infusion preparations, suppositories and the like are used. They can be prepared by commonly known methods. In other words, tablets, capsules, powders, granules or troches can be prepared by formulating appropriate combinations of Compound (I) and excipients such as starch, mannitol, lactose, or the like, binders such as carboxymethylcellulose sodium, hydroxypropylcellulose, or the like, disintegrators such as crystalline cellulose, carboxymethylcellulose calcium, or the like, lubricants such as talc, magnesium stearate, or the like, and fluidity increasing agents such as light anhydrous silicic acid or the like. In addition, aqueous liquid preparations and injection preparations can be prepared by using the water-soluble property of Compound (I). Suppositories can be prepared by dispersing Compound (I) into a commonly used base material such as cacao butter, synthetic fats and oils, or the like, and solidifying the mixture using common procedures.

Other features of the invention will become apparent in the course of the following description of the exemplary embodiments which are given for illustration of the invention and are not intended to be limiting thereof.

EXAMPLES

Example 1

A small amount of water was added to 10.0 g ($8.26 \times 10^{-2}$ mol) of L-cysteine to make a suspension and the pH was adjusted to 9 by adding an aqueous solution of 2 N sodium hydroxide. To this solution, 11.1 g ($9.1 \times 10^{-2}$ mol) of 5-chloro-1-pentanol was added, followed by stirring for 4 hours at 60–70°C. Upon completion of the reaction, extraction with ether was carried out 3 times, the pH of the aqueous layer was adjusted to 4 with 10% hydrochloric acid, and the solvent was evaporated under reduced pressure. The residue was repeatedly washed with acetone and then pulverized. The resulting powder was subjected to ion-exchange chromatography (DOWEX-50W) and the fraction which eluted with a 2 N ammonia water was collected and concentrated under reduced pressure. The residue was recrystallized in a water/ethanol mixture and 12.7 g (yield: 74%) of colorless crystals of S-(5-hydroxypentyl)-L-cysteine (Compound No. 1) was obtained.

m.p. 204–207°C. (decomposed).

$1_{H\text{-}NMR}$ ($D_2O$ +DCl) $\delta$ ppm: 1.20–1.84 (6H, m), 2.48–2.76 (2H, m), 3.04–3.24 (2H, m), 3.48–3.72 (2H, m), 4.34 (1H, m).

Example 2

10.0 g ($8.26 \times 10^{-2}$ mol) of L-cysteine was suspended in a small amount of water and the pH of the solution was adjusted to 9 with an aqueous solution of 2N sodium hydroxide. 13.1 g ($9.1 \times 10^{-2}$ mol) of 6-chloro-1-hexanol was then added and the solution was stirred for 6 hours at 60–70°C. Upon completion of the reaction, ether extraction was carried out 3 times. The pH of the aqueous layer was adjusted to 4.45 with 10% hydrochloric acid and the solution was left standing overnight. The crystals which precipitated out were filtered, rinsed, and recrystallized with water. The resulting material was 11.3 g (yield: 62%) of colorless scale-shaped crystals of S-(6-hydroxyhexyl)-L-cysteine, Compound No. 2 of the present invention.

m.p. 207–209°C. (decomposed).

$1_{H\text{-}NMR}$ ($D_2O$ +DCl) $\delta$ ppm: 1.00–1.80 (8H, m), 2.40–2.76 (2H, m), 3.04–3.18 (2H, m), 3.40–3.72 (2H, m), 4.20–4.44 (1H, m).

Example 3

13.2 g (yield: 64%) of colorless crystals of S-(8-hydroxyoctyl)-L-cysteine (Compound No. 3) was obtained by reacting 10.0 g ($8.26 \times 10^{-2}$ mol) of L-cysteine and 15.42 g ($9.1 \times 10$ mol) of 8-chloro-1-octanol in the same way as described in Example 2.

m.p. 206–208°C. (decomposed).

$1_{H-NMR}$ (D$_2$O +DCl) δ ppm: 0.80–1.80 (12H, m), 2.44–2.76 (2H, m), 3.04–3.28 (2H, m), 3.44–3.72 (2H, m), 4.20–4.48 (1H, m).

Example 4

2.0 g (1.65×10$^{-2}$ mol) of L-cysteine was suspended in a small amount of water and the pH of the suspension was adjusted to 9 with an aqueous solution of 2N sodium hydroxide. 18 ml of ethanol and 4.7 g (1.82×10$^{-2}$ mol) of 5-tosyloxy-1-pentanol were then added and the resulting mixture was stirred all night at room temperature.

Upon completion of the reaction, the pH was adjusted to 4 with 10% hydrochloric acid and the solvent was evaporated under reduced pressure. The residue was pulverized after repeated washing with acetone-chloroform. The resulting powder was subjected to ion-exchange chromatography (Dowex-50W) and eluted with 2 N ammonia water. The fraction which eluted was collected and concentrated under reduced pressure. The residual material was recrystallized in water-ethanol to obtain 2.46 g (yield: 72%) of colorless crystals of S-(5-hydroxypentyl)-L-cysteine (Compound No. 1).

Example 5

The compounds of the present invention were prepared from the raw material, compounds (II), shown in Table 2, in the same manner as in Examples 1–4.

TABLE 2

| Raw Material Compound (II) | Compounds of this Invention Compound (I) |
|---|---|
| 7-chloro-1-heptanol | S—(7-hydroxyheptyl)-L-cysteine |
| 9-chloro-1-nonanol | S—(9-hydroxynonanyl)-L-cysteine |
| 10-bromo-1-decanol | S—(10-hydroxydecanyl)-L-cysteine |
| 11-bromo-1-undecanol | S—(11-hydroxyundecanyl)-L-cysteine |
| 12-bromo-1-dodecanol | S—(12-hydroxydodecanyl)-L-cysteine |
| 13-bromo-1-tridecanol | S—(13-hydroxytridecanyl)-L-cysteine |
| 14-chloro-1-tetradecanol | S—(14-hydroxytetradecanyl)-L-cysteine |
| 15-chloro-1-pentadecanol | S—(15-hydroxypentadecanyl)-L-cysteine |
| 16-chloro-1-hexadecanol | S—(16-hydroxyhexadecanyl)-L-cysteine |
| 17-chloro-1-heptadecanol | S—(17-hydroxyheptadecanyl)-L-cysteine |
| 18-bromo-1-octadecanol | S—(18-hydroxyoctadecanyl)-L-cysteine |
| 19-chloro-1-nonadecanol | S—(19-hydroxynonadecanyl)-L-cysteine |
| 20-chloro-1-eicosanol | S—(20-hydroxyeicosanyl)-L-cysteine |
| 5-iodo-2-pentanol | S—(4-hydroxypentyl)-L-cysteine |
| 6-iodo-3-hexanol | S—(4-hydroxyhexyl)-L-cysteine |
| 7-iodo-2-heptanol | S—(4-hydroxyheptyl)-L-cysteine |

FORMULATION EXAMPLES

Example 6 (tablets)

Tablets were prepared using known procedures and the following ingredients. These tablets can be prepared into film coated or sugar coated tablets.

| Compound No. 1 | 250 mg |
|---|---|
| Crystalline cellulose | 50 mg |
| Lactose | 40 mg |
| Hydroxypropylcellulose | 15 mg |
| Magnesium stearate | 5 mg |
| Total | 360 mg/tablet |

Example 7 (capsules)

Granules were prepared using known procedures and the following ingredients, and then filled into No. 1 capsules.

| Compound No. 2 | 125 mg |
|---|---|
| Crystalline cellulose | 87 mg |
| Light anhydrous silicic acid | 35 mg |
| Talc | 3 mg |
| Total | 250 mg/capsule |

Example 8 (granules)

Granules were prepared according to known procedures using the following ingredients.

| Compound No. 3 | 250 mg |
|---|---|
| Lactose | 600 mg |
| Starch | 135 mg |
| Polyvinylpyrrolidone | 15 mg |
| Total | 1,000 mg |

Example 9 (troche)

Troches were prepared according to known procedures using the following ingredients.

| Compound No. 1 | 250 mg |
|---|---|
| Magnesium stearate | 20 mg |
| Polyvinylpyrrolidone | 50 mg |
| Sucrose | 680 mg |
| Total | 1,000 mg/troche |

Example 10 (powder)

Powder was prepared according to known procedures using the following ingredients.

| Compound No. 2 | 250 mg |
|---|---|
| Light anhydrous silicic acid | 30 mg |
| Lactose | 250 mg |
| Starch | 70 mg |
| Total | 600 mg |

Example 11 (syrup)

Syrup was prepared according to known procedures using the following ingredients.

| Compound No. 3 | 200 mg |
|---|---|
| Ethyl paraoxybenzoate | 1 mg |
| Sucrose | 5,000 mg |

Syrup was produced by adding purified water to a volume of 10 ml.

Example 12 (suppositories)

Suppositories were prepared according to known procedures by forming and solidifying after the following ingredients were melted and stirred.

| Compound No. 1 | 250 mg |
|---|---|
| Cacao butter | 1,250 mg |
| Total | 1,500 mg/suppository |

What is claimed is:
1. A hydroxyalkylcysteine derivative of the following formula (I),
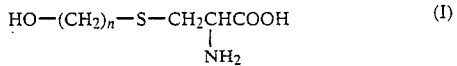
wherein n represents an integer of 5 to 24.
2. An expectorant comprising a hydroxyalkylcysteine derivative of the following formula (I),
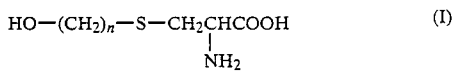
wherein n represents an integer of 5 to 24 and a carrier therefor.
* * * * *